United States Patent [19]
Yamauchi et al.

[11] Patent Number: 5,252,748
[45] Date of Patent: Oct. 12, 1993

[54] RADIOACTIVE IODINE COMPOUND FOR LABELING AN ANTIBODY

[75] Inventors: Akira Yamauchi, Minoh; Akira Ueda, Osaka; Masao Kono, Ibaraki; Kenichi Igano, Nara; Ken Inouye, Kobe, all of Japan

[73] Assignee: Shionogi & Co., Ltd., Osaka, Japan

[21] Appl. No.: 801,810

[22] Filed: Dec. 2, 1991

[30] Foreign Application Priority Data

Nov. 30, 1990 [JP] Japan ................... 2-338871

[51] Int. Cl.$^5$ ................ C07D 207/448; C07K 3/08; C12Q 1/66; C12N 9/96
[52] U.S. Cl. ................ 548/546; 530/391.5; 530/405
[58] Field of Search ............ 548/546; 530/391.5, 530/405

[56] References Cited

U.S. PATENT DOCUMENTS 4,214,098  7/1980  Kitagawa et al. ............ 530/405
4,980,457 12/1990  Jansen et al. ................ 530/405

FOREIGN PATENT DOCUMENTS 0178125 4/1986 European Pat. Off. .
0314127 5/1989 European Pat. Off. .

OTHER PUBLICATIONS

P. C. Srivastava et al., *J. Nuclear Med.* (1990) 31(5):906.

Primary Examiner—David B. Springer
Attorney, Agent, or Firm—Morrison & Foerster

[57] ABSTRACT

The radioactive iodine compound of this invention or an intermediate for preparing the compound is represented by the following formula (I):

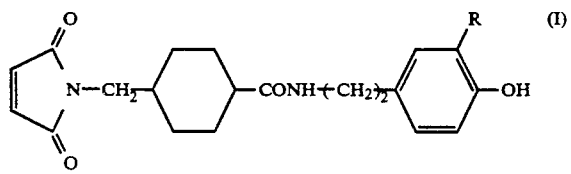

wherein R is H or $^{125}$I.

The radioactive compound can readily introduce a radioactive isotope element such as $^{125}$I into an antibody molecule without damaging the activity of the antibody molecule. Therefore, the compound can preferably be used to label an antibody of immunoradiometric assay, and allow a higher degree of measurement sensitivity.

4 Claims, 4 Drawing Sheets

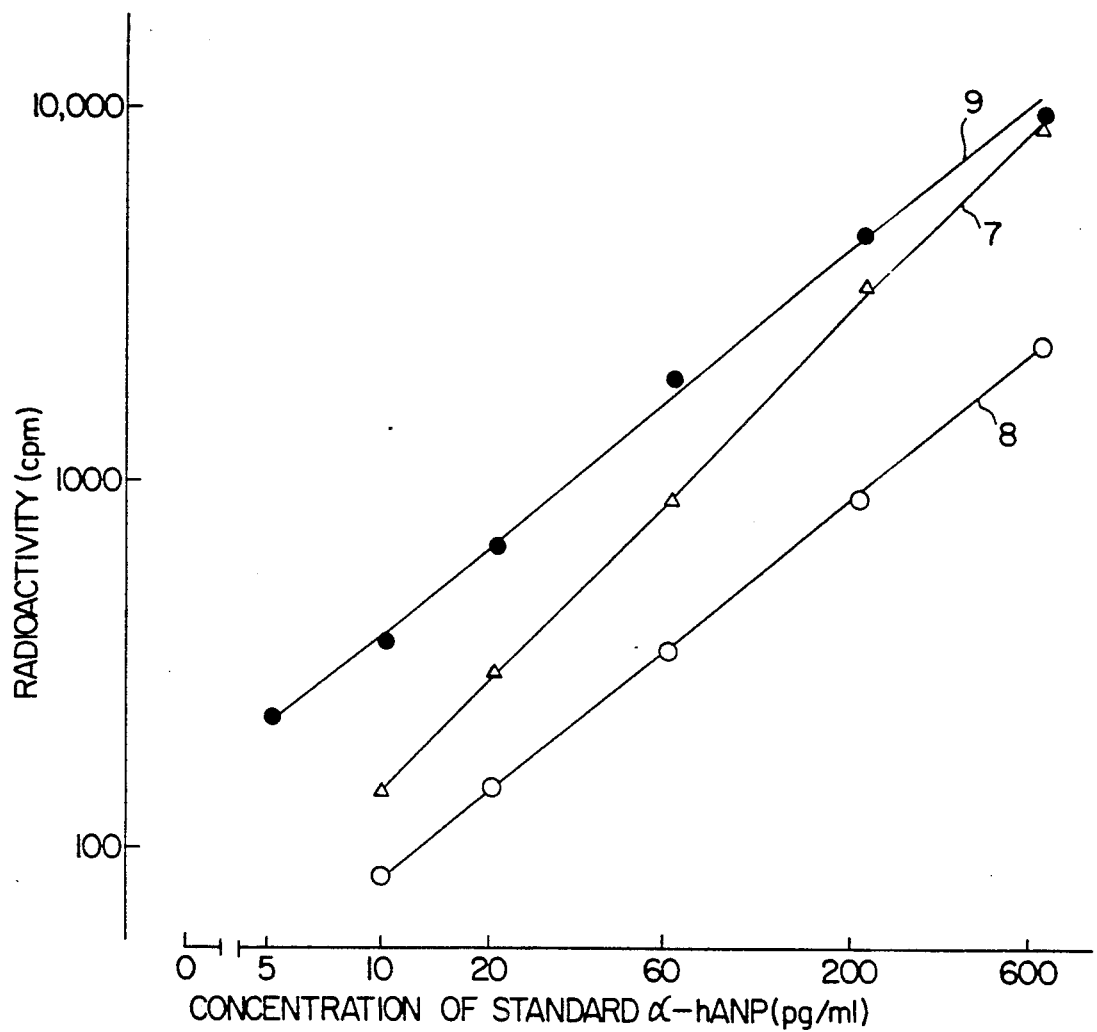
F I G. 4

RADIOACTIVE IODINE COMPOUND FOR LABELING AN ANTIBODY

BACKGROUND OF THE INVENTION

1. Field of the Invention

The present invention relates to a radioactive iodine compound which is used as a labeling reagent for introducing a radioactive isotope element into an antibody molecule in an immunoradiometric assay, and an intermediate for preparing the radioactive iodine compound.

2. Description of the Prior Art

When a protein of interest is detected or quantitatively determined by an antigen-antibody reaction, the antibody is often labeled by a certain material. The assay systems using the labeled antibody include an immunofluorometric assay, an immunoenzymometric assay, an immunoradiometric assay, and the like. For example, the immunoradiometric assay is a method which comprises labeling an antibody with a radioactive isotope element such as $^{125}I$, and measuring the radioactivity of the antigen-antibody complex to determine the amount of the antigen. This method has widely been utilized because a trace amount of antigen can be determined.

Examples of processes for introducing $^{125}I$ into an antibody molecule in the immunoradiometric assay include the chloramine T method, the enzyme method, and the like. According to these methods, for example $Na^{125}I$ is oxidized, and then the resulting free $^{125}I$ is introduced into the Tyr residue present in the antibody molecule. Other methods include Bolton-Hunter reagent method. However, in these methods, some $^{125}I$ may be introduced into the specific binding sites of the antibody, which may reduce the activity of antibody, resulting in a reduction of sensitivity of the measurement.

Other processes for introducing $^{125}I$ into an antibody molecule include those comprising introducing $^{125}I$-containing compounds directly into the antibody molecule. The $^{125}I$-containing compounds include those represented by the following formula (II) (See; P.C. Srivastava et al, J. Nucl. Med., 31(5), 906(1990)):

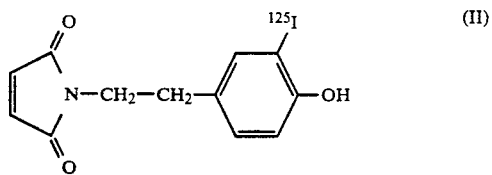

However, this type of compound is relatively unstable. Furthermore, the synthesis of this compound requires some complicated steps.

Labeling reagents that can readily introduce $^{125}I$ into an antibody molecule are required for there have been increasing a demand for detecting or determining protein of interest by using the labeled antibody described above.

SUMMARY OF THE INVENTION

The compound of this invention, which overcomes the above-discussed and numerous other disadvantages and deficiencies of the prior art, is represented by the following formula (I):

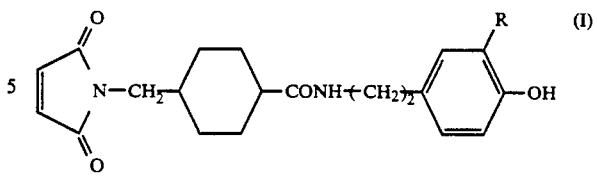

wherein R is H or $^{125}I$.

In a preferred embodiment, R is $^{125}I$, and this compound is used for labeling an antibody.

Thus, the invention described herein makes possible the objectives of (1) providing a radioactive iodine compound that can readily introduce a radioactive isotope element, i.e., $^{125}I$ into an antibody molecule without damaging the activity of the antibody molecule; (2) providing a radioactive iodine compound used as a labeling reagent, which is chemically stable and which can be prepared without complicated steps; (3) providing a radioactive iodine compound that can preferably be used as a labeling reagent of an antibody in an immunoradiometric assay, and allow a highly sensitive measurement; and (4) providing an intermediate for preparing the above-mentioned radioactive iodine compound.

BRIEF DESCRIPTION OF THE DRAWINGS

This invention may be better understood and its numerous objects and advantages will become apparent to those skilled in the art by reference to the accompanying drawings as follows:

FIG. 4 shows standard curves obtained from an immunoradiometric assay of known amount of α-hANP using antibodies which had been labeled with $^{125}I$ by the use of a compound of this invention and by the chloramine T method.

DESCRIPTION OF THE PREFERRED EMBODIMENTS

Figure 1:
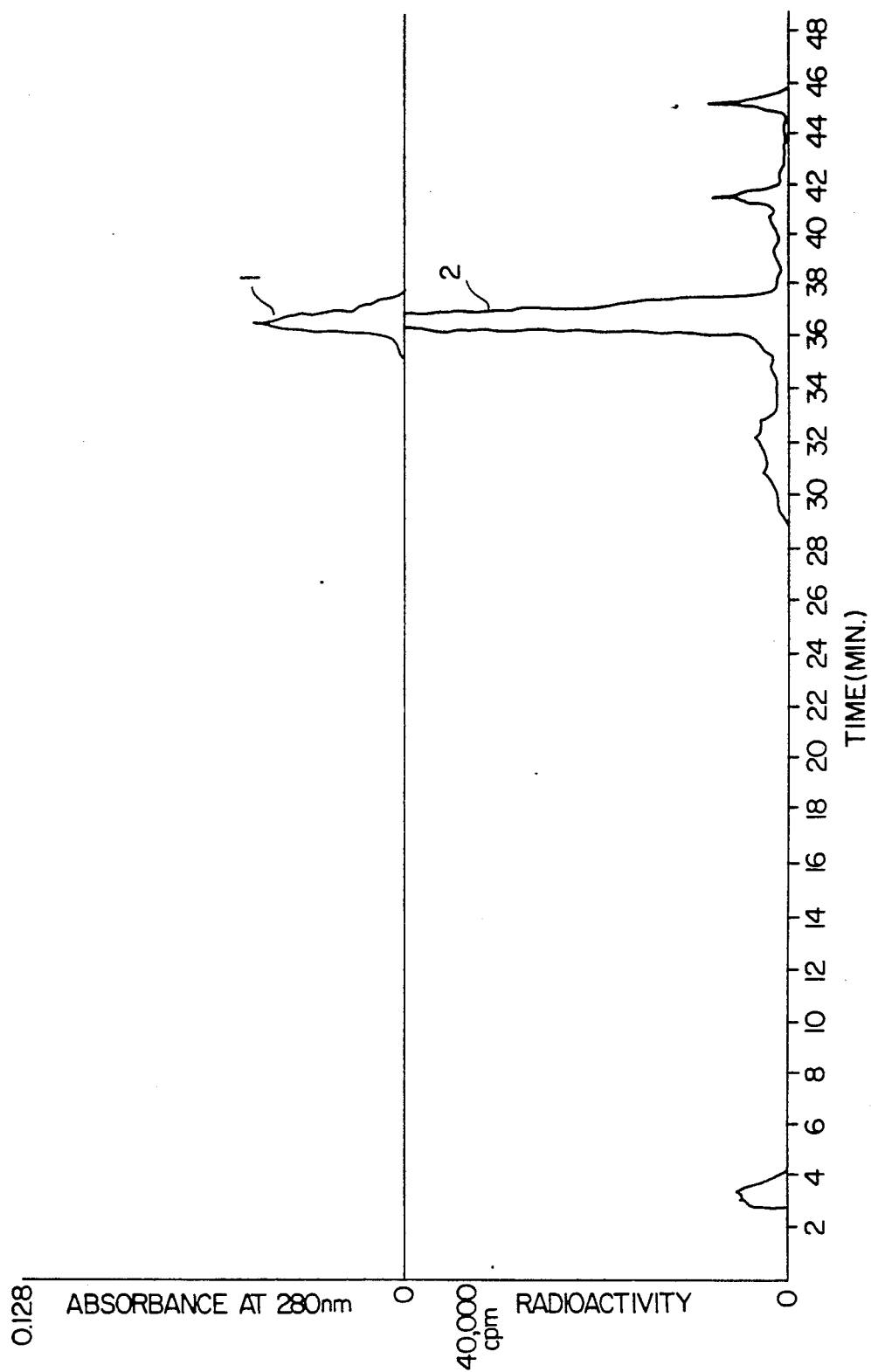
FIG. 1 shows a reverse phase HPLC chromatogram (detected by absorbance at 280 nm) of non-radioactive 4-(N-maleimidomethyl) cyclohexane carboxylic acid-3-iodotyramide in the upper column, and a reverse phase HPLC chromatogram (detected by radioactivity) of radioactive 4-(N-maleimidomethyl) cyclohexane carboxylic acid-3-([$^{125}I$]iodo) tyramide, i.e., a reaction solution of 3-([$^{125}I$]iodo) tyramine and succinimidyl-4-(N-maleimidomethyl) cyclohexane-1-carboxylate (SMCC), in the lower column.

The present invention provides a radioactive iodine compound or an intermediate for preparing the compound represented by the following formula (I):

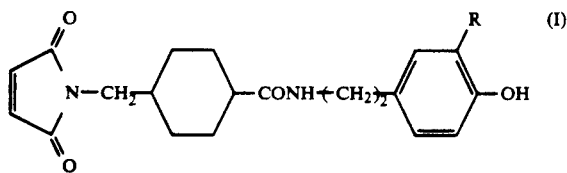

wherein R is H or $^{125}$I.

The radioactive iodine compound of this invention, i.e., 4-(N-maleimidomethyl) cyclohexane-carboxylic acid-3-([$^{125}$I]iodo) tyramide which is preferably used for labeling an antibody is, for example, synthesized by the following procedure.

First, to the methanol solution of tyramine, added are phosphate buffer, Na$^{125}$I, and a chloramine T solution, successively to introduce $^{125}$I into the benzene ring of the tyramine. After a sodium pyrosulfite solution is added to the reaction mixture to terminate the reaction, 3-($^{125}$I)iodotyramine is recovered separately by a reverse phase HPLC.

Then, the 3-($^{125}$I)iodotyramine is added to a phosphate buffer followed by the addition of a dimethylformamide solution of succinimidyl-4-(N-maleimidomethyl) cyclohexane-1-carboxylate to proceed a reaction. The reaction mixture is fractionated by a reverse phase HPLC to obtain the radioactive iodine compound of this invention.

Also, the radioactive iodine compound of this invention is synthesized by the following procedure.

First, to tyramine (i.e., 4-hydroxyphenetylamine), added are succinimidyl-4-(N-maleimidomethyl) cyclohexane-1-carboxylate and 1-hydroxybenzotriazole, and reacted to synthesize 4-(N-maleimidomethyl) cyclohexanecarboxylic acid tyramide. Then, a Na$^{125}$I solution is added to the 4-(N-maleimidomethyl) cyclohexanecarboxylic acid tyramide followed by the addition of a chloramine T solution to introduce $^{125}$I into the benzene ring of the tyramide. The reaction mixture is immediately fractionated by a reverse phase HPLC to obtain the radioactive iodine compound of this invention.

The present invention also includes the above-mentioned 4-(N-maleimidomethyl)cyclohexanecarboxylic acid tyramide, which is preferably used for the synthesis of 4-(N-maleimidomethyl) cyclohexanecarboxylic acid-3-([$^{125}$I]iodo) tyramide.

The resulting radioactive iodine compound of this invention can be reacted with a —SH group under moderate conditions, for example, in pH 6, to form a covalent bond. The disulfide bonds present in the hinge region of an antibody are reduced with a reductant such as mercaptoethylamine to expose —SH groups. When the antibody molecule having these exposed —SH groups is reacted with the radioactive iodine compound of this invention, a complex can readily be obtained, thus introducing a radioactive iodine into the antibody molecule. Since the hinge region is located away from the site which the antigen is bound to, the activity of the antibody is not likely to be interfered.

The method for binding a radioactive iodine compound of this invention to the hinge region of an antibody is applicable for both a monoclonal antibody, and a polyclonal antibody. Moreover, it is also applicable for any form of antibody molecules such as IgG, IgM, IgA, IgE, Fab', and the like. When the radioactive iodine compound of this invention is used as described above, any antibody molecules can be labeled with $^{125}$I.

The resulting complex of the antibody molecule and the radioactive iodine compound, i.e., the antibody labeled with the radioactive iodine compound of this invention, is useful for an immunoradiometric assay.

For example, human α-atrial natriuretic peptide (α-hANP) present in human plasma can be detected or determined when a complex of Fab' of KY-ANP-1 that is a monoclonal antibody against α-hANP and the radioactive iodine compound of this invention is used in an immunoradiometric assay. Since the activity of the antibody is not damaged, the sensitivity of measurement using the complex is higher than that using the antibody molecule labeled by the conventional chloramine T method.

These antibody molecules labeled with the radioactive iodine compound of this invention can be preferably used as labeled antibodies for immunoradiometric assays since their activities are well retained. Particularly, it may preferably be employed for determining a trace amount of protein because of high sensitivity of the measurement.

The present invention is illustrated with reference to examples described below.

EXAMPLE 1

Synthesis of Radioactive Iodine Compound

To 0.01 ml of 7 mg/ml methanol solution of tyramine (Nakarai tesque Co.) in a glass tube, added were 0.05 ml of 0.5 M phosphate buffer (pH 7.5), 0.05 ml of Na$^{125}$I (3.7 GBq/ml; Amersham Co.), and 0.01 ml of 0.2% chloramine T solution successively and stirred at room temperature for 1 minute. Then, 0.01 ml of 1% sodium pyrosulfite solution was added to the reaction mixture to terminate the reaction. The resulting reaction mixture was fractionated by a reverse phase HPLC (column, Nucleosil $_{10}$C$_{18}$; Chemco Co.; inner diameter, 4.6 mm; length, 300 mm; solvent, acetonitrile containing 0.1% trifluoroacetic acid) to isolate 150 MBq of 3-([$^{125}$I]iodo)tyramine.

The 150 MBq of the 3-([$^{125}$I]iodo)tyramine was added to 0.05 ml of 0.1 M phosphate buffer (pH 7.0) followed by the addition of 0.01 ml of 7 mg/ml N,N-dimethylformamide solution of succinimidyl-4-(N-maleimidomethyl) cyclohexane-1-carboxylate (SMCC; Pierce Co.) and stirred at room temperature for 1 hour. The resulting reaction mixture was fractionated by a reverse phase HPLC under the conditions described above to obtain 110 MBq of 4-(N-maleimidomethyl) cyclohexanecarboxylic acid-3-([$^{125}$I]iodo) tyramide which is the radioactive iodine compound of this invention.

This radioactive iodine compound was identified by using the non-radioactive 4-(N-maleimidomethyl) cyclohexanecarboxylic acid-3-iodotyramide which was prepared by the procedure described infra in Referential Example 1. FIG. 1 shows a reverse phase HPLC chromatogram (detected by absorbance at 280 nm) of the non-radioactive 4-(N-maleimidomethyl) cyclohexanecarboxylic acid-3-iodotyramide in the upper column, and a reverse phase HPLC chromatogram (detected by radioactivity) of the 4-(N-maleimidomethyl) cyclohexanecarboxylic acid-3-([$^{125}$I]iodo) tyramide, i.e., a reaction solution of 3-([$^{125}$I]iodo) tyramine and SMCC, in the lower column. It can be seen from FIG. 1 that peak 2 which is located in the same elution point as peak 1 of non-radioactive 4-(N-maleimidomethyl)

cyclohexanecarboxylic acid-3-iodotyramide corresponds to the radioactive iodine compound of this invention.

REFERENTIAL EXAMPLE 1

Synthesis of Non-radioactive 4-(N-maleimidomethyl) cyclohexanecarboxylic acid-3-iodotyramide a) Synthesis of 3-iodotyramide.$CF_3COOH$ First, 300 mg (2.2 mmol) of tyramine was dissolved into 10 ml of $CH_3OH$ followed by the addition of 0.475 ml of 28% $CH_3ONa/CH_3OH$ (2.2 mmol of $CH_3ONa$), and a $CH_3OH$ (6 ml) solution of 560 mg (2.2 mmol) $I_2$ and stirred at room temperature for 15 minutes. Then, 0.4 ml of 12% aqueous solution of sodium pyrosulfite was added to the reaction mixture to terminate the reaction.

After the solvent was evaporated under reduced pressure, 100 ml of ethyl acetate, and 30 ml of water were added to the residue, and the resulting precipiate was removed by filtration. The filtrate was concentrated, and purified by a reverse phase HPLC (column, YMC S-50 120A ODS, AM-type; length, 200 mm; inner diameter, 30 mm; solvent, 0–40% $CH_3CN/0.1\%$ $CF_3COOH$, 2000 ml, linear concentration gradient). The purified filtrate was crystallized by using a mixed solvent of $CH_3OH$/ethyl acetate/petroleum ether, and then recrystallized to obtain the desired product having a melting point of 177°–178° C. with 291 mg (35%) yield.

| Elementary Analysis Values $C_8H_{10}NOI.CF_3COOH$ | | | |
| --- | --- | --- | --- |
| Theoretical Values (%) | C, 31.85; | H, 2.94; | N, 3.71; |
| | I, 33.65; | F, 15.11 | |
| Observed Values (%) | C, 32.17; | H, 3.15; | N, 3.64; |
| | I, 33.35; | F, 14.93 | | b) Synthesis of 4-(N-maleimidomethyl) cyclohexanecarboxylic acid-3-iodotyramide

First, 186 mg (0.49 mmol) of the 3-iodotyramide.$CF_3COOH$ obtained in the item a) above was dissolved into 2 ml of N,N-dimethylformamide followed by the addition of 0.17 ml (0.98 mmol) of N,N-diisopropylethylamine, and 66 mg (0.49 mmol) of 1-hydroxybenzotriazol. Then, 165 mg (0.49 mmol) of succinimidyl-4-(N-maleimidomethyl) cyclohexane-1-carboxylate was added to this solution, and reacted together at room temperature for 1 hour. Then, after the solvent was distilled off under reduced pressure, the residue was dissolved into ethyl acetate. The solution was washed successively with 1 M HCl, and water, and dried on magnesium sulfate. After the evaporation of the solvent, the residue was crystallized in ethyl acetate, and recrystallized in $CH_3OH$ to obtained the desired product having a melting point (decomposition point) of 204°–206° C. with 107 mg yield (45%).

| Elementary Analysis Values $C_{20}H_{23}N_2O_4I.\frac{1}{2}H_2O$ | | | |
| --- | --- | --- | --- |
| Theoretical Values (%) | C, 49.19; | H, 4.89; | N, 5.47; |
| | I, 25.99 | | |
| Observed Values (%) | C, 49.20; | H, 4.90; | N, 5.79; |
| | I, 26.20 | | |

EXAMPLE 2

Synthesis of 4-(N-maleimidomethyl) cyclohexanecarboxylic acid-tyramide

First, 82.3 mg of 4-hydroxyphenetylamine was dissolved into 4 ml of dimethylformamide followed by the addition of 200 mg (0.6 mmol) of succinimidyl-4-(N-maleimidomethyl) cyclohexane-1-carboxylate, and 81.1 mg (0.6 mmol) of 1-hydroxybenzotriazol to react together at room temperature for 60 minutes. After the evaporation of the solvent under reduced pressure, the residue was dissolved into 30 ml of ethyl acetate, washed with 10 ml of 0.5 M HCl, and three portions of 15 ml water, and dried on magnesium sulfate. After the evaporation of the solvent, the crystallized residue was recrystallized in a mixed solvent of chloroform/methanol to obtain the desired compound having a melting point of 211°–212.5° C. with 113 mg yield (52%).

| Elementary Analysis Values $C_{20}H_{24}N_2O_4.\frac{1}{2}H_2O$ | | | |
| --- | --- | --- | --- |
| Theoretical Values (%) | C, 66.28; | H, 6.67; | N, 7.73 |
| Observed Values (%) | C, 66.40; | H, 6.73; | N, 7.73 |

Synthesis of Radioactive Iodine Compound

First, 1 mg of the 4-(N-maleimidomethyl) cyclohexanecarboxylic acid tyramide was dissolved into dimethyl sulfoxide (Wako Pure Chemical Industries Co.) to form 1 ml of solution. The solution was divided into 0.05 ml portions and stored at −20° C. or less. Then, 0.015 ml of the solution containing 15 μg (41 nmol) of the compound described above was transferred into a glass tube followed by the addition of 0.04 ml of 0.2 M phosphate buffer (pH 7.0), and 0.04 ml (148 MBq) of the solution containing $Na^{125}I$ (IMS-30; Amersham Co.) and mixed. To the mixture, added was 0.01 ml (7.1 nmol) of 0.05% chloramine T solution and stirred for 30 seconds.

Then, after the addition of 0.05 ml of acetonitrile containing 0.1% trifluoroacetic acid and mixing, the reaction mixture was fractionated by a reverse phase HPLC (column, Nucleosil $_{10}C_{18}$; Chemco Co.; inner diameter, 4 mm; length, 300 mm; solvent, a mixed solvent of acetonitrile containing 0.05% trifluoroacetic acid/methanol/water at a ratio of 30:20:50) to obtain 114 MBq of 4-(N-maleimidomethyl) cyclohexane-carboxylic acid-3-([$^{125}$I]iodo) tyramide which is the radioactive iodine compound of this invention.

EXAMPLE 3

Immunoradiometric Assay

The following examples illustrate the application of the radioactive iodine compound prepared in Example 1 to the immunoradiometric assay of human α-natriuretic peptide (α-hANP).

a) Preparation of KY-ANP-1.Fab'

First, 1 ml of ascites obtained by the administration of mouse anti-α-hANP-bovine thyroglobulin [BTG] antibody-producing hybridoma (KY-ANP-1; See, Japanese Laid-Open Patent Publication No. 1-061500) into a mouse was purified in an affinity column (Affi-Gel ® Protein A MAPS-II; Bio-Rad Co.) to obtain 2.9 mg of KY-ANP-1 IgG. Then, 2 mg of this IgG was added to 0.1 M acetate buffer (pH 4.2) containing 0.1 M sodium chloride. To this solution added was 0.08 mg of a pepsin derived from swine gastric mucosa (Boehringer Mannheim Co.), and incubated at 37° C. for 16 hours. Then, 0.02 ml of 2 M tris-hydrochloric acid buffer (pH 8.0) was added to the reaction mixture, and subjected to a gel-filtration (column, Ultrogel® AcA44, IBF Co., 1.5×55 cm; solvent, 0.1 M phosphate buffer containing 5 mM ethylenediaminetetraacetic acid (EDTA) (pH 6.0)) to obtain 1.1 mg of F(ab')$_2$ of KY-ANP-1.

Then, 0.3 mg of the F(ab')$_2$ was added to 0.1 ml of 0.1 M phosphate buffer (pH 6.0) containing 5 mM EDTA followed by the addition of 0.01 ml of 0.1 M mercaptoethylamine solution (Nakarai tesque Co.), and incubated at 37° C. for 1.5 hours. The reaction mixture was subjected to a HPLC (column, TSK-GEL G2000 SW$_{XL}$, Tosoh Co., 0.75×30 cm; solvent, 0.1 M phosphate buffer containing 5 mM EDTA (pH 6.0)) to recover 0.19 mg of KY-ANP-1 Fab' fraction.

b) $^{125}$I labeling of KY-ANP-1 Fab'

First, 60 μg (1.3 nmol) of the KY-ANP-1.Fab', and 93 MBq (1.3 nmol) of the radioactive iodine compound as prepared in Example 1 were added to 0.12 ml of 0.1 M phosphate buffer containing 5 mM EDTA (pH 6.0), and incubated at room temperature for 1 hour. To the reaction mixture, added was 0.02 ml of 1% S-carboxymethylated bovine serum albumin solution, mixed, and subjected to a gel-filtration (PD-10 Pharmacia Co.) to obtain 80 MBq of a complex of KY-ANP-1.Fab' and the radioactive iodine compound of this invention. The complex was used as a $^{125}$I labeled antibody for the following immunoradiometric assay.

c) Preparation of Antibody Beads

IgG of mouse anti-α-hANP (17-28)-BTG antibody, AN111 (See, Japanese Laid-Open Patent Publication No. 2-276591) was added to 0.01 M phosphate buffer containing 0.1 M sodium chloride (pH 7.0) at a concentration of 25 μg/ml. Then 50 ml of this solution was added to 400 polystyrene beads (particle size, 6.4 mm, Precision Plastic Ball Co.), and allowed to stand at 4° C. for 24 hours. These beads were washed, and treated with 0.1% solution of bovine serum albumin to obtain antibody beads.

d) Immunoradiometric Assay

Figure 2:
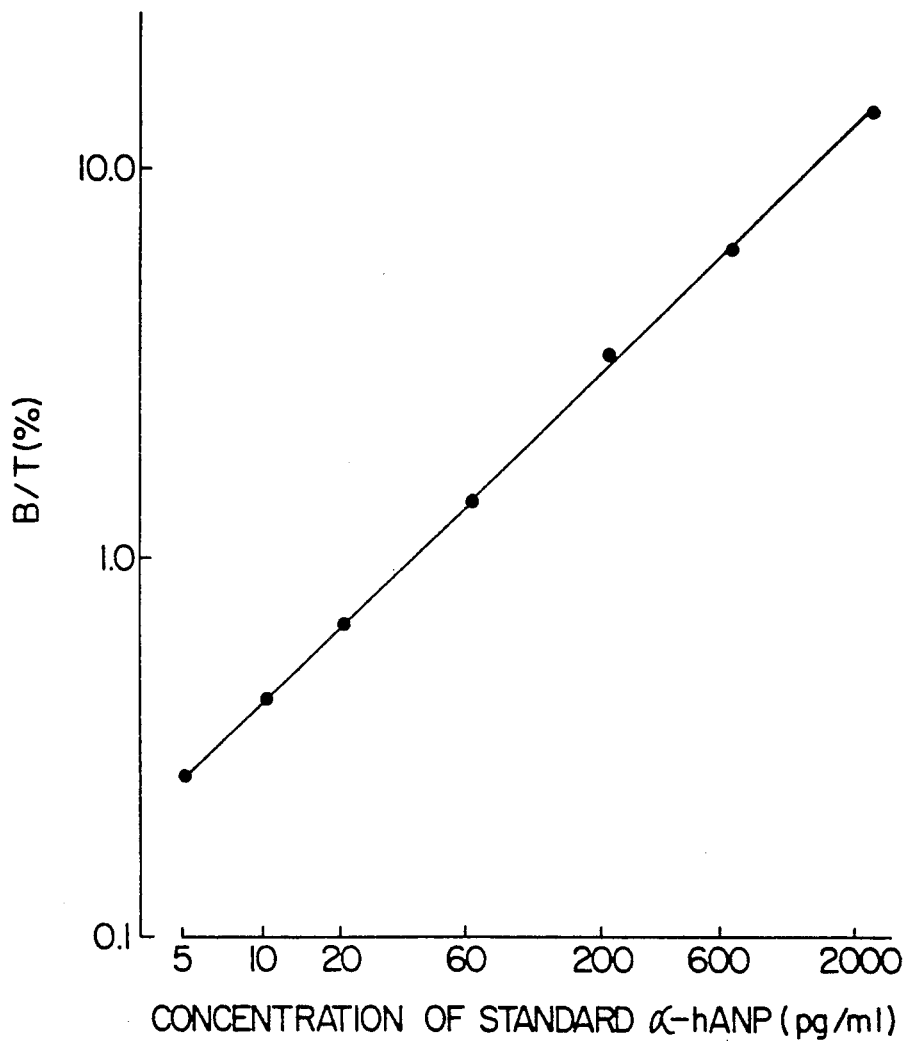
FIG. 2 shows a standard curve obtained from an immunoradiometic assay of known amount of α-hANP using KY-ANP-1.Fab' which had been labeled with $^{125}I$ by the use of radioactive iodine compound of this invention.

First, 0.1 ml of standard α-hANP solution (concentration, 5-2000 pg/ml), and 0.2 ml of assay buffer (0.1 M phosphate buffer (pH 7.0) containing 1 mM EDTA.2Na, 0.2 mM cystine dihydrochloride, 0.1% sodium azide, 0.3 M sodium chloride, $10^3$ KIU/ml aprotinin, and 0.1% bovine serum albumin) were taken into a polystyrene tube followed by the addition of one antibody bead obtained in item c) above, and incubated at 4° C. for 24 hours. After removing the supernatant by aspiration, the antibody bead was washed twice with 1 ml of washing solution, i.e., 0.1 M phosphate buffer saline (pH 7.0) containing 0.1% Tween 20 (trade name). To the antibody bead, 0.3 ml of the assay buffer solution containing $^{125}$I labeled antibody prepared in the item b) above at a concentration of 5×10$^5$ cpm/ml was added, and then incubated at 4° C. for 24 hours. After washing the reacted antibody bead twice with 1 ml of the washing solution, the radioactivity of the $^{125}$I labeled antibody bound to the polystyrene bead was measured by a gamma counter. The concentration of the standard α-hANP solution in a horizontal axis, and the binding rate, B/T (%), which is a ratio of bound radioactivity to the total radioactivity added, calculated from the radioactive value (cpm) measured by the gamma counter in a vertical axis, were plotted to illustrate a standard curve shown in FIG. 2. The minimum detectable concentration of the standard α-hANP solution was 2 pg/ml.

Figure 3:
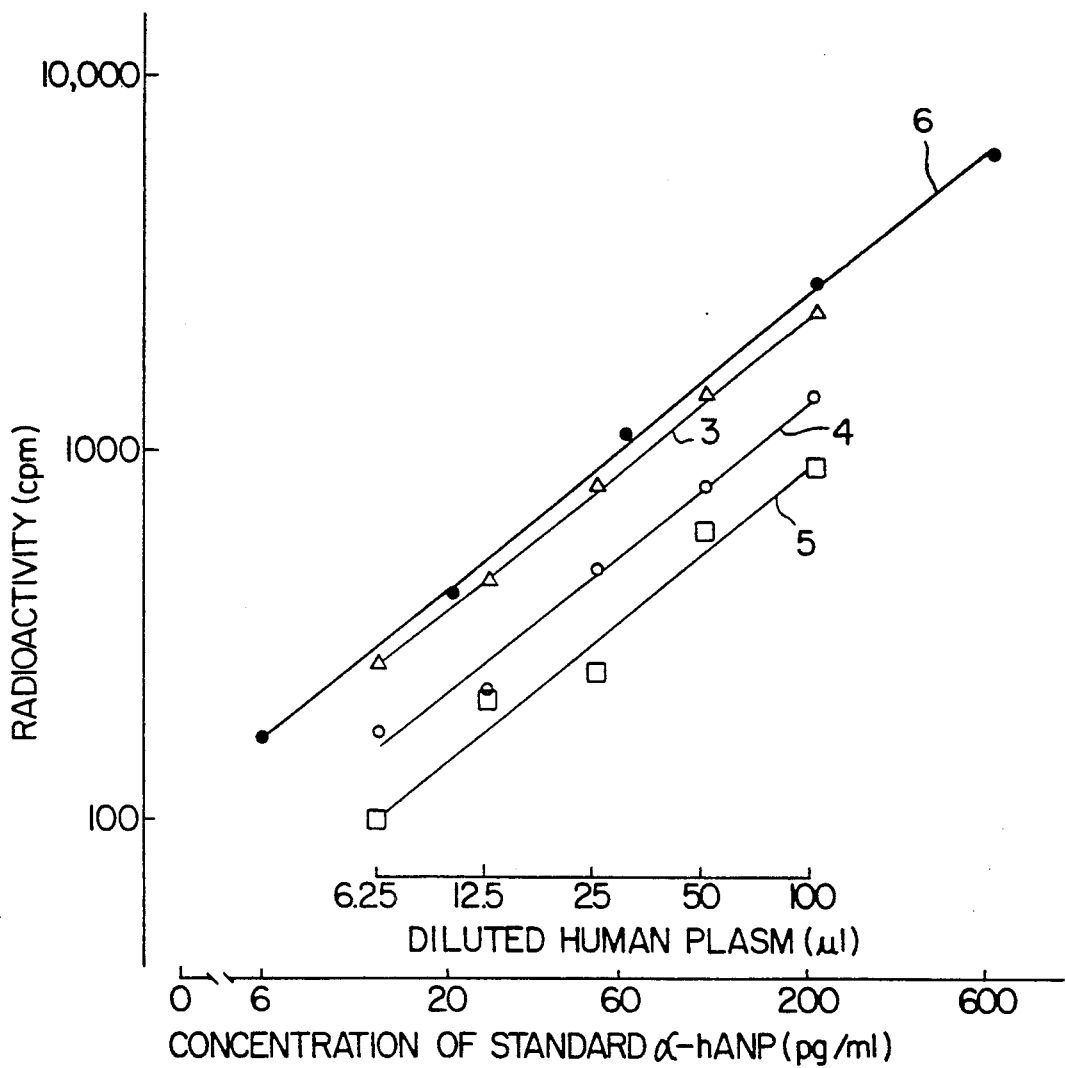
FIG. 3 shows graphs, each showing relationship between as volume of plasma and radioactivity obtained when α-hANP in human plasma is measured by immunoradiometric assay using KY-ANP-1.Fab' which had been labeled with $^{125}I$ by the use of a radioactive iodine compounds of this invention.

Also, the same immunoradiometric assay was performed as described above except that three serially diluted human plasma samples were used instead of the standard α-hANP solution. FIG. 3 shows the plots (curves 3-5) obtained from measurements of the diluted human plasma samples and the standard curve (curve 6). It can be seen from FIG. 3 that the curves 3-5 are well paralleled with the standard curve.

e) Determination of α-hANP Concentration in Human Plasma

The α-hANP concentrations of twenty six healthy adult plasma samples were measured by the aforementioned immunoradiometric assay. According to Table 1 which illustrates the results of the measurement, the α-hANP concentrations were 2 to 53 pg/ml with an average and standard deviation of 16.6±12.6 pg/ml. Eleven samples had 10 pg/ml or less of α-hANP concentration any of which were able to be measured by the immunoradiometric assay.

TABLE 1

| Sample | Age | sex | Concentration of α-hANP (pg/ml) | (pmol/L) |
|---|---|---|---|---|
| 1 | 54 | M | 16 | 5.2 |
| 2 | 30 | M | 37 | 11.9 |
| 3 | 49 | M | 19 | 6.1 |
| 4 | 54 | M | 18 | 5.8 |
| 5 | 52 | M | 16 | 5.3 |
| 6 | 39 | M | 8 | 2.6 |
| 7 | 40 | M | 15 | 4.8 |
| 8 | 52 | M | 20 | 6.5 |
| 9 | 25 | M | 7 | 2.3 |
| 10 | 36 | M | 8 | 2.7 |
| 11 | 46 | M | 5 | 1.7 |
| 12 | 51 | M | 2 | 0.7 |
| 13 | 48 | M | 17 | 5.6 |
| 14 | 53 | M | 36 | 11.6 |
| 15 | 41 | M | 3 | 1.0 |
| 16 | 50 | M | 3 | 1.1 |
| 17 | 48 | M | 9 | 3.0 |
| 18 | 31 | M | 8 | 2.5 |
| 19 | 30 | F | 16 | 5.2 |
| 20 | 41 | F | 13 | 4.4 |
| 21 | 24 | F | 21 | 6.7 |
| 22 | 39 | F | 53 | 17.2 |
| 23 | 23 | F | 42 | 13.5 |
| 24 | 22 | F | 10 | 3.3 |
| 25 | 27 | F | 21 | 6.9 |
| 26 | 23 | F | 7 | 2.2 |
| Mean ± S.D. | | | 16.6 ± 12.6 | 5.4 ± 4.1 |

1) Sex: M, male; F, female

COMPARATIVE EXAMPLE 1

Using $^{125}$I labeled antibodies of KY-ANP-1.IgG and Fab' by the chloramine T method instead of the antibody labeled with the radioactive iodine compound of this invention, the immunoradiometric assay was performed as described in item d) of Example 3, and the standard curves was obtained, which are shown in FIG. 4. It can be seen from FIG. 4 that when the $^{125}$I labeled antibodies of IgG and Fab' obtained by the chloramine T method (corresponding to curves 7 and 8, respectively) were used, the minimum limit of detection was high, i.e., more than 10 pg/ml, compared to that using the antibody labeled with the radioactive iodine compound of this invention (curve 9), indicating lower sensitivity of the assay using an antibody labeled by chloramine T method.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A compound represented by the following formula (I):

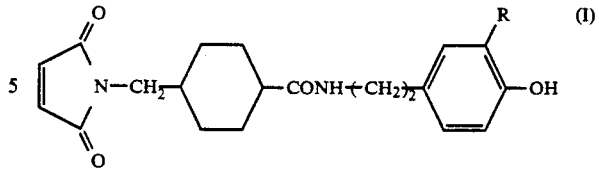

wherein R is H or $^{125}I$.

2. A compound of claim 1 wherein R is $^{125}I$.

3. A method for introducing an isotope element $^{125}I$ into an antibody molecule comprising, reacting an antibody with an SH group with a compound of claim 2.

4. A method of claim 3 wherein the antibody molecule is selected from the group consisting of IgG, IgM, IgA, IgE and Fab'.

* * * * *